United States Patent [19]

Kornblum et al.

[11] 4,019,515

[45] Apr. 26, 1977

[54] ENEMATA ADMINISTERING DEVICE

[76] Inventors: Daniel Kornblum, 4606 W. Central Ave., Toledo, Ohio 43615; John S. Efroymson, 5154 Saddlecreed Road, Toledo, Ohio 43623

[22] Filed: Dec. 8, 1975

[21] Appl. No.: 638,337

[52] U.S. Cl. .............................. 128/246; 128/2 A; 128/349 B

[51] Int. Cl.² .................... A61B 6/00; A61M 25/00

[58] Field of Search .... 128/2 R, 2 A, 246, 348–351

[56] References Cited

UNITED STATES PATENTS

| 397,060 | 1/1889 | Knapp | 128/246 |
|---|---|---|---|
| 2,813,531 | 11/1957 | Lee | 128/350 R |
| 3,459,175 | 8/1969 | Miller | 128/246 X |
| 3,707,151 | 12/1972 | Jackson | 128/351 |
| 3,889,676 | 6/1975 | Greene | 128/246 |

Primary Examiner—Dalton L. Truluck
Attorney, Agent, or Firm—McAulay, Fields, Fisher & Goldstein

[57] ABSTRACT

A dual balloon retention and positioning arrangement in an enemata administering device. Both balloons are mounted on the stem. The first balloon, internal of the patient, is air inflated. The second balloon, external of the patient, is in communication with the interior of the stem and is automatically inflated by the applied barium sulphate suspension fluid when the fluid is flowed through the stem to the patient.

11 Claims, 3 Drawing Figures

U.S. Patent
April 26, 1977
4,019,515
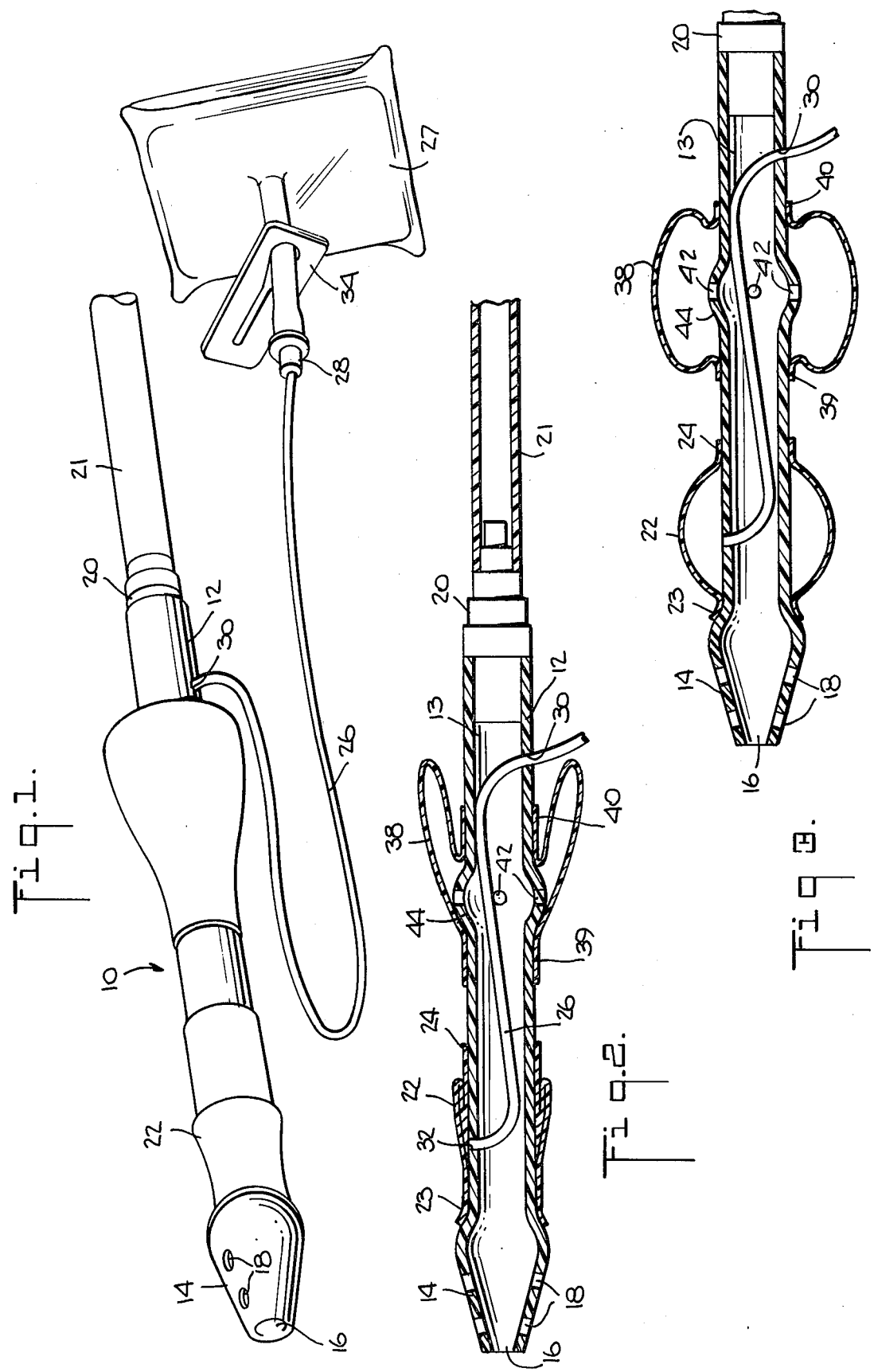

ENEMATA ADMINISTERING DEVICE

Background of the Invention

This invention relates to devices for giving enemata, and, particularly to a device which provides an improved, more comfortable and more effective retention arrangement to prevent leaking at minimum discomfort to the patient.

Enemata devices are known and used for many purposes. Applicant is particularly familiar with the use of such devices to place a barium sulphate suspension in the colon of the patient during X-ray examination. It is well known to place an inflatable annular balloon near the end which is inserted in the patient (i.s. the distal end). The balloon is deflated when inserted and inflated after insertion to preclude premature expulsion of the tip and of the fluid. It is further known to use pads or secondary inflatable balloons positioned on the enemata device outside the patient.

Such catheters employing an interior as well as a posterior inflatable annular balloon provide an interaction which holds the interior balloon against the anal opening to prevent the barium sulphate suspension from draining or leaking out of the patient around the catheter tube. U.S. Pat. No. 3,154,077, issued on Oct. 27, 1964, illustrates one such inflatable balloon device.

As contrasted with the single balloon device, the double balloon devices are appreciably more expensive because of the need for a second inflation system. Furthermore, the double balloon device provides complications to the administering personnel in that proper inflation of two separate balloons, in an appropriate sequence, and without overinflation has to be undertaken.

Accordingly, it is a purpose of this invention to provide a catheter having a retention arrangement which will more effectively prevent leakage when in use.

It is a further purpose of this invention to provide this more effective seal for the catheter without requiring additional attention or manipulation on the part of the administering personnel.

The more effective the annular balloon is as a seal, the more it tends to be uncomfortable for the patient. Thus it is another purpose of this invention to provide an improved trade off between comfort and sealing effectiveness.

It is a further purpose of this invention to provide the above two purposes in a construction which is relatively economic so that it is economically feasible to provide the improved function and improve patient comfort.

Further, because of the requirements for a disposable enemata apparatus and thus for minimal costs, it is a further purpose of this invention to provide the above objectives in a device that is as similar as possible to currently known devices and which can be manufactured easily and inexpensively.

BRIEF DESCRIPTION

Briefly, in the embodiment disclosed herein, there is the usual hollow stem having exit ports and a fluid inlet. A first inflatable annular balloon is positioned immediately behind the tip and is inflated though an airway. The airway communicates with the interior of the balloon through an opening in the sidewall of the stem under this first balloon. The airway extends back through the stem to a source of air. Operator control of the source of air effects inflation of this balloon.

Rearward of this first balloon is a second annular balloon. The second balloon is sealed to the stem and is in communication with the interior of the stem through four openings in the stem. As barium suspension is flowed into the patient through the stem, the suspension will also flow through these four openings to inflate the second balloon. Thus the second ballon is inflated when, and only when, barium fluid is applied to the patient. Furthermore, the degree of inflation of the second balloon is a direct function of the pressure of the barium fluid in the patient.

The inflation of the second balloon exerts a pressure against the patient which tends to draw the catheter stem outwardly so that the inflated first balloon will seat more completely against the patient's sphincter. This improved seating of the first balloon effects improved sealing. The force of the seating is a direct function of the extent of second balloon inflation and thus a direct function of the pressure of the fluid. Accordingly, there is an automatic relationship between the force of the seating of the first balloon and the pressure that causes the barium fluid to tend to leak.

The term barium is used in the art and herein as a short hand term for barium sulphate suspension.

Brief Description of the Drawings

FIG. 1, is a perspective view of the device of this invention.

FIG. 2., is a longitudinal cross-sectional view through the stem of the FIG. 1 device.

FIG. 3, is a view similar to that of FIG. 2 showing both balloons inflated.

DETAILED DESCRIPTION OF THE PREFERRED EMBODIMENTS

The FIGS. all relate to a single embodiment of the enemata device 10. As shown therein, there is a smooth, flexible, plastic tubular enema stem 12 having a hollow interior 13. The stem includes a distal or forward end tip portion 14 of conventional shape such as a tapered bulbular form. The tip 14 is provided with a primary exit opening 16 at the extreme distal end and secondary exit ports 18 through the sides of the tip. The entire back portion of the stem is cylindrical and terminates in an arrangement 20 at the rear or proximal end which can be adapted to receive a flexible tube 21 from a fluid supply such as a barium sulphate suspension container (not shown). The stem 12 is formed of a suitable plastic material such as polyvinylchloride which is readily molded into the desired shape.

A first expandable resilient balloon 22, preferably made of latex, is mounted on the enterior of the stem 12. This balloon 22 is preferably in the form of a sleeve and is described in greater detail in U.S. Pat. No. 3,889,676 issued June 17, 1975. The balloon 22 is sealed at ends 23 and 24 to spaced apart zones around the stem 12. An airway provides a conduit for air into the interior of the first balloon 22. An air syringe 27 of a conventional sort is coupled at coupling 28 to the airway 26. The airway 26 extends into the stem 12 at a back opening 30 and extends through the stem 12 to a front opening 22 in a stem at which opening 32 there is communication with the interior of the first balloon 22. A clamp 34 can be used by the operator to keep the balloon inflated. When inflated this balloon 22 acts to retain the catheter 10 in the patient.

FIG. 3 illustrates the first balloon 22 in an inflated form. After the device is inserted into a patient and the balloon 22 is then inflated, its exact contour will be determined by the body tissue it contacts and thus FIG. 3 is simply an idealized and simplified indication of inflation.

A second balloon 38 is mounted on the stem 12 rearward of the first balloon. This second balloon 38 is annular and sealed at ends 39 and 40 to spaced apart zones around the stem 12. Four ports 42 communication between the interior of the second balloon 38 and the stem interior 13.

The first balloon 22 is preferably sleeve like as shown because that is a more comfortable configuration for insertion and withdrawal from the patient. The first balloon 22 is positioned inside the patient. However, the second balloon 38 is located outside the patient when the enema device 10 is positioned in the patient and thus can have the bulkier configuration shown.

The two inflatable annular balloons 22 and 38 are positioned apart by a distance such that when inflated, they exert some degree of compressive force, in an axial direction, on the patient's tissues. As a consequence, when the second balloon 38 is inflated, it tends to draw or pull the inner or first balloon 22 backward against the patient's interior tissues thereby providing a more effective sealing of the anal opening by the inner balloon 22.

An annular ridge 44 serves the purpose of providing an initial stop or limit to the insertion of the catheter into the patient. On initial insertion both balloons 22 and 38 are deflated and this annular ridge 44 is a useful limiting stop on insertion. The four ports 42 are through the ridge 44 for convenience. Four ports are preferred to assure unhindered flow of liquid into the outer balloon 38.

It is preferred that the inner balloon 22 have the sleeve like configuration shown when deflated so that upon insertion patient discomfort is minimized. However, it is preferred that the outer balloon 38 have the bulbous shape shown, when deflated, so as to provide sufficient elastomer material to expand uniformly and adequately under the normal range of pressures applied by the barium liquid suspension.

In use, the administrator inserts the device 10 in the patient with both balloons 22 and 38 deflated. Once the device 10 is positioned, the administrator then actuates the source of air to provide air inflation of the inner balloon 22 through the airway 26. The inner balloon 22 when inflated then operates as the usual retention balloon.

When the administrator applies a barium suspension, the fluid flows through the stem interior 13 into the patient and at the same time flows through the ports 42 to provide liquid inflation of the second or outer balloon 38. As this outer balloon 38 inflates the liquid, it presses against the patient's outer tissues and tends to draw back the stem 12 so that the air inflated inner balloon 22 is drawn against the patient's inner tissues. This creates a more effective seal against leaking at precisely the moment when the increased sealing effectiveness is required. Thus, the patient is saved the discomfort of the dual balloon seal prior to the time when the sealing function is required. Furthermore, the inflation of the outer balloon 38 is automatic and does not require additional manipulation by the administrator. A second airway is not required, a second source of air is not required and a second valving or shut off clamp is not required.

Because there is a continuous fluid system of barium sulphate suspension from the barium within the patient through the barium within the stem interior 13 to the barium reservoir (not shown), the pressure of the liquid in the outer balloon 38 is a function of the pressure throughout the liquid system. Thus, the greater the pressure within the patient, the greater the pressure within the outer balloon 38 and the greater will be the inflation of the balloon 38. The result is that as balloon 38 inflation increases, the more firmly will it cause the inner balloon 22 to seat. In this fashion, the greater the requirement for an effective seal to prevent liquid leakage, the greater will be the force of seating and thus the more effective will the seal be. And this will all occur in an automatic fashion because of the fact that the pressure of the liquid in the outer balloon 38 is a function of the pressure of the liquid within the patient.

After the X-ray or flouroscope of the patient has been taken, the draining of the barium sulphate suspension will automatically deflate the outer balloon 38 thereby minimizing discomfort to the patient as soon as there is no longer a need for the more effective sealing.

The barium ports 42 are relatively large compared to the air port 32 to permit ready flow of barium into the annular balloon 38. Thus ports 42 approximately six millimeters in diameter have been used. It has been found useful to space the balloons 22, 38 from one another by about an inch as measured when inflated. That is, the free space between the inflated balloon is in the order of 1 inch. This is less than the normal length of the anal canal and assures a tight fit. But because of the ability of the inflatable latex balloons 22, 38 to adjust discomfort is minimized.

What is claimed is:

1. In an enemata administering device having a hollow stem with an exit port at a first end thereof and an inlet at the second end thereof, the improvement comprising:
   a first inflatable and deflatable annular retention balloon sealed across a portion of the stem near the forward end thereof,
   an airway extending to a first post in the stem under said first balloon to provide inflation and deflation of said first balloon, and
   a second inflatable and deflatable annular balloon sealed across a portion of the stem rearward from said first balloon,
   said stem having a second port providing communication between the interior of said stem and the interior of said second balloon,
   said second balloon inflating solely when liquid is flowed through said stem, and said first balloon inflating solely when fluid is forced through said airway,
   when said balloons are so inflated, said second balloon automatically conforming to a patient's external anatomy and causing the inflated first balloon to be held in a sealing position within the patient.

2. The improvement of claim 1 further comprising: means to apply a barium sulphate fluid suspension at the inlet of said stem.

3. The improvement of claim 1 wherein:
   said stem has a plurality of ports providing communication between the inteior of said stem and the interior of said second balloon to provide rapid and substantially uniform expansion of said balloon.

4. The improvement of claim 2 wherein:
said stem has a plurality of ports providing communication between the interior of said stem and the interior of said balloon to provide rapid and substantailly uniform expantion of said balloon.

5. The improvement of claim 1 wherein:
said first balloon has the configuration of a reentrant sleeve when deflated.

6. The improvement of claim 4 wherein:
said first balloon has the configuration of a reentrant sleeve when deflated.

7. The improvement of claim 1 wherein:
said second balloon has a bulbous shape when deflated.

8. The improvement of claim 5 wherein:
said second balloon has a bulbous shape when deflated.

9. The improvement of claim 6 wherein:
said second balloon has a bulbous shape when deflated.

10. In an enemata administering device having a hollow stem with an exit port at a front end thereof and an inlet at the back end thereof, the improvement comprising:
retention means to retain said device in a patient against forces tending to expel said device,
an inflatable and deflatable annular balloon sealed across a portion of the stem rearward from said retention means,
said stem having a port providing communication between the interior of said stem and the interior of said balloon,
said balloon inflating solely when liquid is flowed through said stem,
when said balloon is so inflated, said balloon automatically conforming to a patient's external anatomy and causing said retention means to be held in a sealing position within the patient.

11. The improvement of claim 10 wherein: said stem has a plurality of ports providing communication between the interior of said stem and the interior of said balloon to provide rapid and substantially uniform expansion of said balloon.

* * * * *